United States Patent
Retzlaff et al.

(10) Patent No.: US 6,844,934 B2
(45) Date of Patent: Jan. 18, 2005

(54) OPTICAL TURBIDIMETER WITH A LENS TUBE

(75) Inventors: Gregory S. Retzlaff, Menomonee Falls, WI (US); John R. Woodward, Hartford, WI (US); Terry L. Dickey, Pflugerville, TX (US); Karl King, Germantown, WI (US)

(73) Assignee: Hach Company, Loveland, CO (US)

( * ) Notice: Subject to any disclaimer, the term of this patent is extended or adjusted under 35 U.S.C. 154(b) by 0 days.

(21) Appl. No.: 10/478,226
(22) PCT Filed: May 21, 2002
(86) PCT No.: PCT/US02/16049
§ 371 (c)(1), (2), (4) Date: Nov. 20, 2003
(87) PCT Pub. No.: WO02/095454
PCT Pub. Date: Nov. 28, 2002

(65) Prior Publication Data
US 2004/0145742 A1 Jul. 29, 2004

Related U.S. Application Data
(60) Provisional application No. 60/292,829, filed on May 23, 2001.

(51) Int. Cl.[7] .............................. G01N 21/00
(52) U.S. Cl. ...................................... 356/436; 356/440
(58) Field of Search .................................. 356/436–440

(56) References Cited

U.S. PATENT DOCUMENTS

| | | | |
|---|---|---|---|
| 4,619,530 A | 10/1986 | Meserol et al. | 356/440 |
| 5,140,168 A | 8/1992 | King | 250/575 |
| 5,586,567 A | 12/1996 | Smith et al. | 134/57 D |

Primary Examiner—Gregory J. Toatley, Jr.
Assistant Examiner—Amanda Merlino
(74) Attorney, Agent, or Firm—George E. Haas; Quarles & Brady LLP

(57) ABSTRACT

An apparatus for measuring tubidity of a liquid has a tubular lens of transparent material with an aperture for receiving the liquid. First and second first light emitters are positioned adjacent the tubular lens to produce two beams of light each diverging at a predefined angle and impinging the tubular lens. The tubular lens refracts the diverging beams of light from the two light emitters into separate collimated beams within the aperture. A first light detector positioned adjacent the tubular lens diametrically opposite to the first light emitter and a second light detector positioned diametrically opposite to the first light emitter and a second light detector positioned diametrically opposite to the second light emitter. Each light detector produces a signal indicating an intensity of light received from within the tubular lens and the signals are process to derive a turbidity measurement.

16 Claims, 3 Drawing Sheets

OPTICAL TURBIDIMETER WITH A LENS TUBE

CROSS-REFERENCE TO RELATED APPLICATIONS

This application claims benefit of U.S. Provisional Patent Application No. 60/292,829 filed May 23, 2001.

BACKGROUND OF THE INVENTION

1. Field of the Invention

The present invention relates to apparatus for measuring turbidity of liquids, and more particularly to optical devices which utilize light emitters and detectors to sense the turbidity.

2. Description of the Related Art

Turbidity is an optical characteristic of a liquid that is related to the presence, nature and amount of suspended matter or particles which scatter light in an otherwise pure liquid. Turbidity may be sensed by instruments commonly known as turbidimeters, which measure the characteristics in terms of the amounts of light that are transmitted and scattered by the liquid.

U.S. Pat. Nos. 5,059,811 and 5,140,168 disclose a turbidimeter that utilizes two light sources and two detectors in which each detector is aligned with a different light source. Each light source is energized alternately, and the amounts of light detected by the aligned and unaligned detectors are compared. The liquid under analysis flows through a baffle assembly which blocks stray light from entering the light detectors. The detector signals, produced when each light source is energized, are processed to derive a turbidity value as defined by the U.S. Environmental Protection Agency. Various photoelectric instruments permit turbidity measurements to be conducted on static liquids, or those which flow continuously between the emitters and detectors.

Previous turbidimeters use point light sources, such as a bulb or a light emitting diode (LED) to generate a light beam that is transmitted through the liquid sample in a sensing cavity. Light emerges from a point source in rays that diverge. Those diverging light rays can be reflected by the surfaces of the sensing cavity onto the light detectors, thereby producing signals that are unrelated to the turbidity of the liquid sample being measured. That extraneous light produces what is referred to as stray light error. It is desirable to minimize the stray light error and thus increase the accuracy of the turbidity measurement.

SUMMARY OF THE INVENTION

The present turbidimeter has a transparent tube with an aperture for receiving the liquid. The optical characteristics of the transparent tube provide a lens tube that receives divergent light rays from a point source of light, such as a light emitting diode (LED). Upon passing through that lens tube, the light rays are refracted according to Snell's Law into a collimated beam. That is, a light ray is changed in direction according to the ratio of the indices of refraction of the two materials at a lens interface. The turbidimeter has two interfaces at the lens tube: air/lens and lens/liquid. Therefore the material of the lens tube and the liquid being examined affect how the light rays are directed and have to be taken into account in designing the lens tube turbidimeter.

A first light emitter is positioned adjacent the lens tube to produce a beam of light which diverges at a predefined angle and impinges the lens tube. A first light detector is positioned adjacent the lens tube diametrically opposite to the first light emitter to produce a signal indicating an intensity of light traveling in a straight line through the liquid from the first light emitter. A second light detector is positioned adjacent the lens tube to produce a signal indicating an intensity of light from the first light emitter which is scattered upon traveling through the liquid. The lens tube refracts that diverging beam of light into a collimated beam within the aperture, and then refracts light from within the aperture onto each of the first and second light detectors.

Another aspect of the present invention enables the light beam from the light emitter to diverge at a relatively large angle in order to send a relatively wide light beam through the liquid. In this case, a lens is placed between the light emitter and the lens tube to redirect the light beam to strike the lens tube at a predefined angle of incidence. This predefined angle of incidence is selected so that the lens tube will collimate the widely diverging light beam into a non-diverging beam within the liquid.

In the preferred embodiment of the turbidimeter, a second light emitter is located adjacent the lens tube diametrically opposite the second light detector. The second light emitter produces a light beam that diverges at a given angle and impinges the lens tube. The lens tube refracts that light beam into another collimated beam within the aperture.

DETAILED DESCRIPTION OF THE INVENTION

Figure 1:
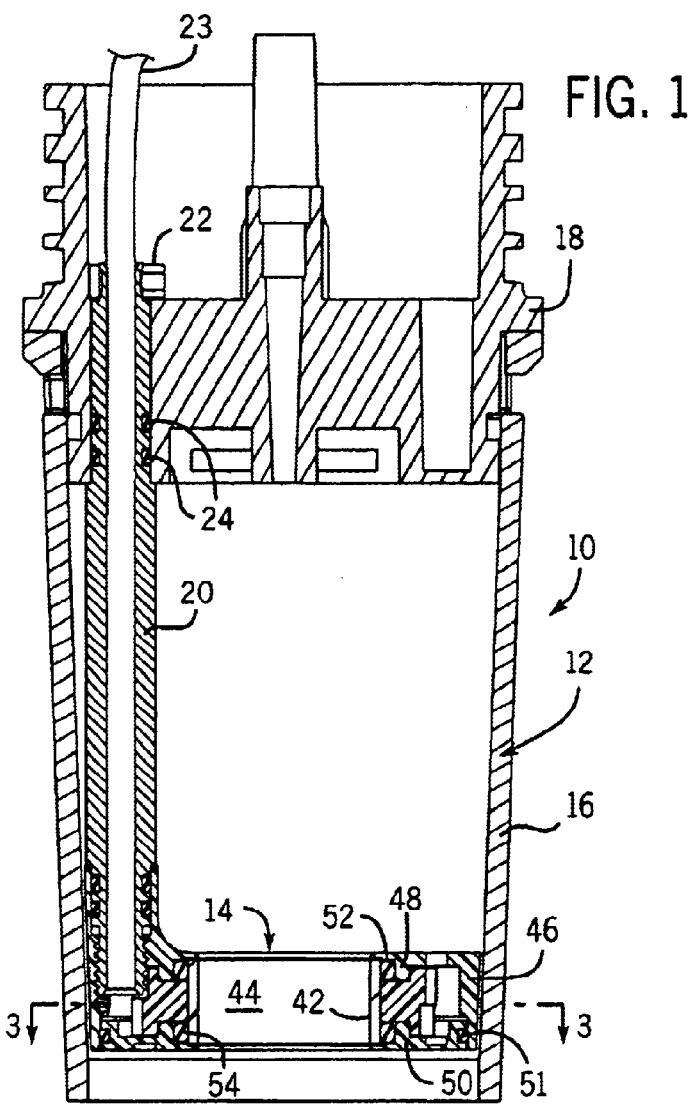
FIG. 1 is a cross-section through a first embodiment of a turbidimeter sensor assembly according to the present invention.

With initial reference to FIG. 1, a turbidimeter 10 comprises a container 12 which encloses a sensor assembly 14. The container 12 is formed by an outer tube 16 that tapers slightly inward from the upper end to the lower end with the upper end being closed by a cap 18. The sensing assembly 14 fits within the inner opening of the outer tube 16 and is wedged against the tapered interior wall. A stainless steel, wire conduit 20 of the sensing assembly 14 extends upwardly through an aperture in the cap 18. A cam retainer 22 engages and secures the upper end of the wire conduit 20 against the inside surface of the cap 18. Two O-rings 24 extend around the conduit providing a water tight seal with the cap 18.

Figure 2:
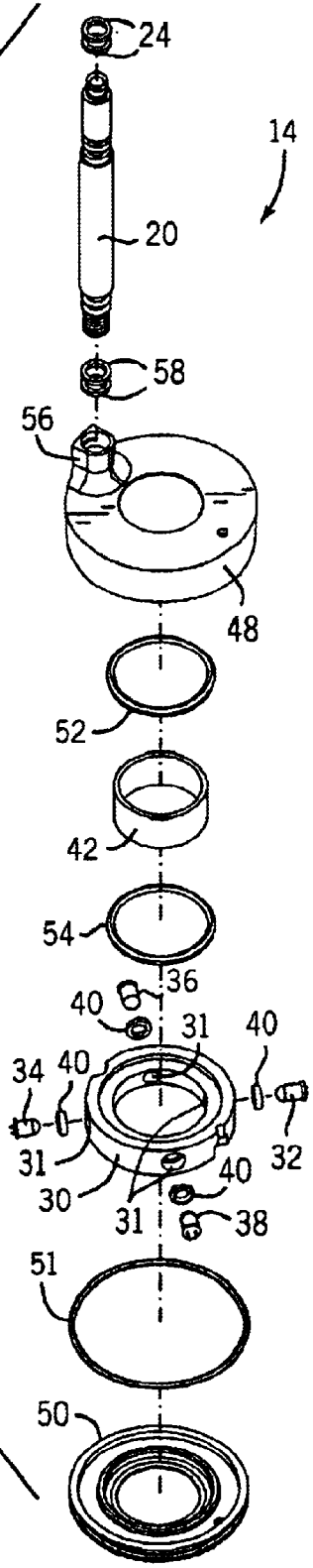
FIG. 2 is an exploded view of the turbidimeter sensor assembly.
Figure 3:
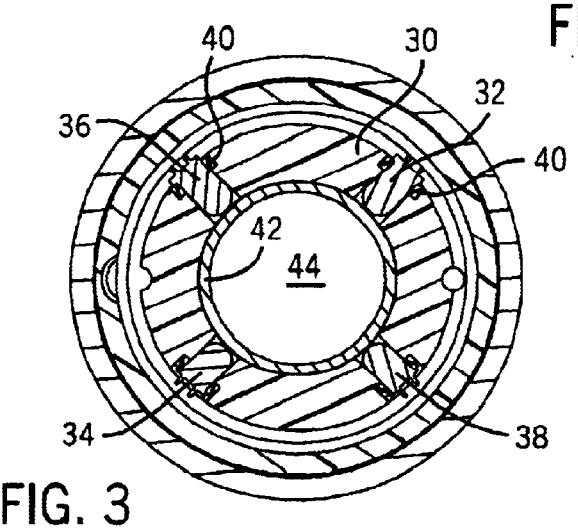
FIG. 3 is a cross-sectional view taken along line 3—3 of FIG. 1.

With reference to FIG. 2, the sensor assembly 14 has a mounting ring 30 fabricated of a black polycarbonate material. As shown in greater detail in FIG. 3, the mounting ring 30 has four holes spaced radially at 90 degree increments. Within a first set of diagonally opposed apertures 31 are a first light emitter 32, such as a first light emitting diode (LED) and first light detector 34. A second light emitter 36 is located in one of the other two diametrically opposed apertures 31, with a second light detector 38 in the other of those apertures. The two emitters 32 and 36 act as a point source producing light rays at a wavelength of 860 nm, for example, which diverge from the emitter at a fixed angle, for example six degrees as determined by the manufacturer of that component. Each of the emitters and detectors is held within its respective aperture 31, by a resilient retaining ring 40. Thus, there are two emitter and detector pairs mounted in the sensor assembly 14.

A transparent lens tube 42 is located within the central opening of the mounting ring 30 and forms an passage 44 through the sensor assembly 14. The lens tube 42 preferably is made of a material, such as quartz, glass or sapphire, which is highly scratch resistant so as to inhibit abrasion by particles in the liquid being examined. The sections of the lens tube 42 in front of each light emitter 32 and 36 collimate the light output into a beam that is directed toward the diametrically opposed light detector 34 and 36, respectively. The sections of the lens tube 42 in front of each light detector 34 and 36 focus the impinging light beam onto the active surface of the adjacent detector.

As noted previously the light rays diverge from the point source emitters 32 and 36 at a predefined angle, six degrees for example. The optical characteristics of the transparent lens tube 42 directs the diverging light rays from the LED into a collimated (non-divergent) beam through the liquid contained in the tube. Upon passing through the lens tube 42 the light rays from the LED are refracted according to Snell's Law. That is, a ray is changed in direction according to the ratio of the indices of refraction of the two materials at the lens interface. There are two interfaces at the lens tube: air/lens and lens/liquid. The material of the lens tube and the particular liquid being examined affect how the light rays are directed.

Figure 4:
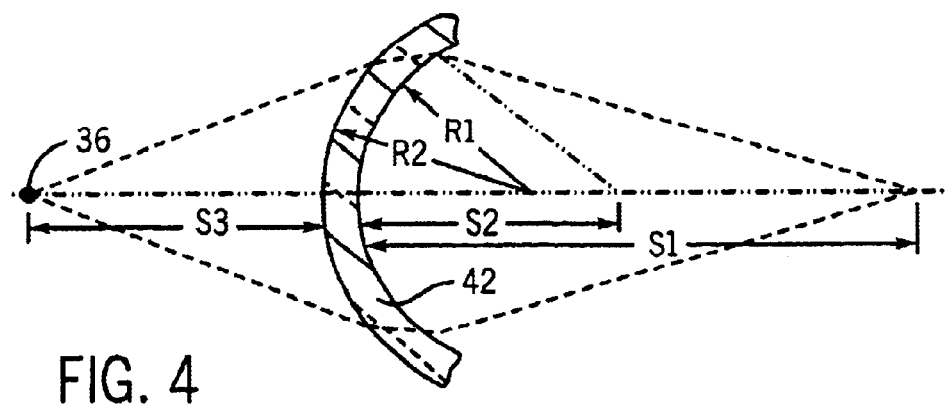
FIG. 4 depicts the optics of the turbidimeter sensor assembly.

The optics of the sensor assembly 14 are depicted in FIG. 4. The light emitter 36 is positioned at a distance S3 from the outer diameter of the lens tube 42. That lens tube has an inner radius R1 and an outer radius R2 with a thickness d there between. The inner surface of the lens tube has a focal length S2. The standard lens equations are:

$$\frac{n1}{S1} - \frac{n2}{S2-d} = \frac{n1-n2}{R1}$$

$$\frac{n2}{S2} - \frac{n3}{S3} = \frac{n2-n3}{R2}$$

where n1 is the index of refraction of the liquid being examined, n2 is the index of refraction of the transparent lens tube 42, and n3 is the index of refraction of material outside the lens tube (e.g. air). In order to produce parallel light rays within the lens tube 42, i.e. S1 equals infinity, the distance S3 is given by solving the above equations for S3 which yields the equation:

$$S3 = \frac{n3R2\,[n2R1+(n2-n1)d]}{n2R2(n2-n1)-(n2-n3)[(n2R1+(n2-n1)d]}$$

The same equations are used to derive the distance that each light detector 34 and 38 is located from the lens tube 42, so that the curvature of the lens tube focuses the non-divergent light rays in the liquid onto the respective light detector. In the simplest embodiment, each light detector is placed the same distance from the outer diameter of the lens tube as the light source. However, it should be understood that the light detector 34 and 36 sense light that impinges on an area of each device and thus each light detector is placed slightly less that the distance S3 from the lens tube so that a spot of light appears on the sensing area. By using the curvature of the lens tube to direct the lights rays into parallel paths, separate lenses are not required in front of each light emitter and detector.

The mounting ring 30 is encased in an outer housing 46 formed by an upper member 48 and a bottom cover 50, both fabricated of black polyvinyl chloride (PVC). The upper member 48 has a flat annular top surface with a circular flange extending downwardly there from and around the mounting ring 30 and lens tube 42. The bottom cover 50 snaps inside the flange to form the outer housing 46. In the fabricated sensor assembly 14, an upper O-ring 52 provides a water tight seal between the outer perimeter of the lens tube 42 and the upper housing member 48. A lower O-ring 54 provides a similar seal between the outer perimeter of the lens tube 42 and the lower cover 50, as seen in FIG. 1. The upper housing member 48 has an upwardly extending coupling 56 with a threaded aperture into which a threaded lower end of the wire conduit 20 is received. Two O-rings 58 provide a water tight seal between those components. An O-ring 51 provides a water tight seal between the upper housing member 48 and the lower cover 50.

To measure turbidity of a liquid, the turbidimeter 10 is dipped into the liquid which is allowed to flow upward through the central passage 44 of the sensor assembly 14 and into the outer tube 16. Then an electronic control circuit, connected to the turbidimeter 10 via cable 23, selectively activates each of the emitters 32 and 36 and processes the signals produced by the light detectors 34 and 38.

Figure 5:
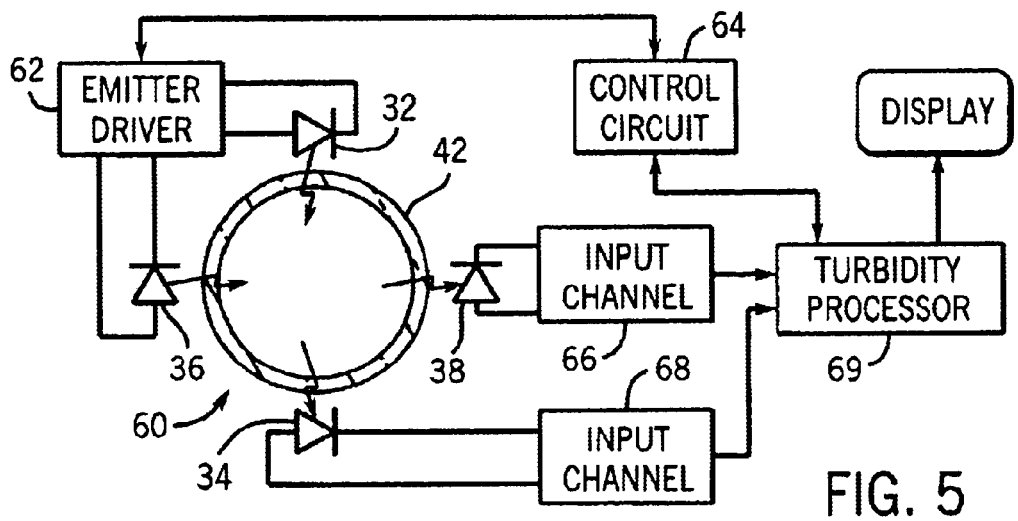
FIG. 5 is a schematic diagram of electronic circuit for operating the turbidimeter and producing a turbidity measurement.

With reference to FIG. 5, the light emitters 32 and 36 are powered by a circuit 60 that includes an emitter driver 62 that is controlled by a microcomputer based control circuit 64. The control circuit 64 has an internal memory which stores the software program for operating the turbidimeter, as well as storing data used and generated by that program. Each light detector 34 and 38 is connected to one of two identical input channels 66 and 68, each having amplifier stages, signal filters and a synchronous detector similar to the circuit described in U.S. Pat. No. 5,140,168, which is incorporated herein by reference. The output signal from the input channels 66 and 68 corresponds to the intensity of the light sensed by the associated light detector 34 or 38.

The unknown liquid contained in the sensor assembly passage 44 is measured by alternately modulating each light emitter 32 and 36. By modulating each light emitter and then synchronously detecting the light signals from the detectors, components in those signals from sources other than the emitters are rejected. While each emitter is active, the signals from the two light detectors 35 and 38 are read by the turbidity processor 69 and stored in memory as light input values for the transmitted and scattered light. The signal from the light detector that is aligned with the presently active emitter represents the intensity of light transmitted directly through the unknown liquid. The non-aligned light detector produces a signal which represents the intensity of light that is scattered by material in the unknown liquid. The resultant light input values then are processed by well known techniques, such as described in the patent cited immediately above, to produce a measurement of the turbidity of the liquid.

Figure 7:
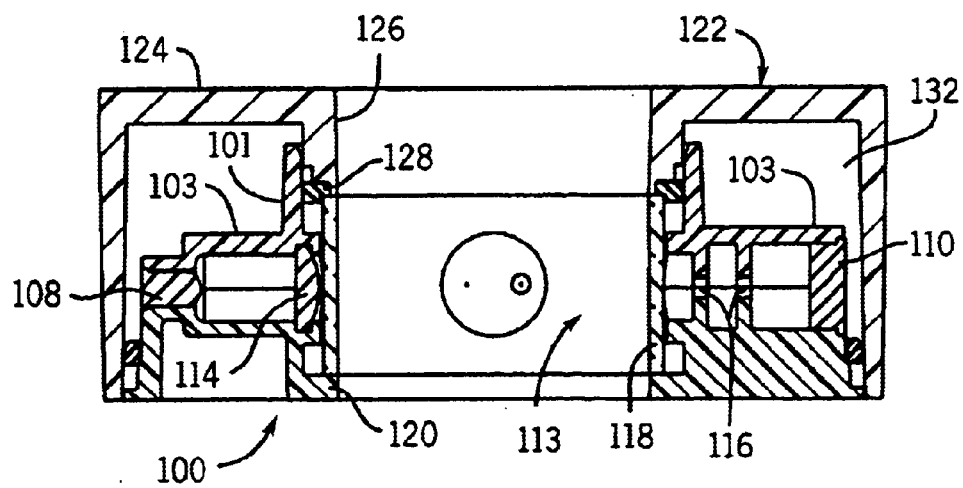
FIG. 7 is an cross-sectional view through the second embodiment.
Figure 6:
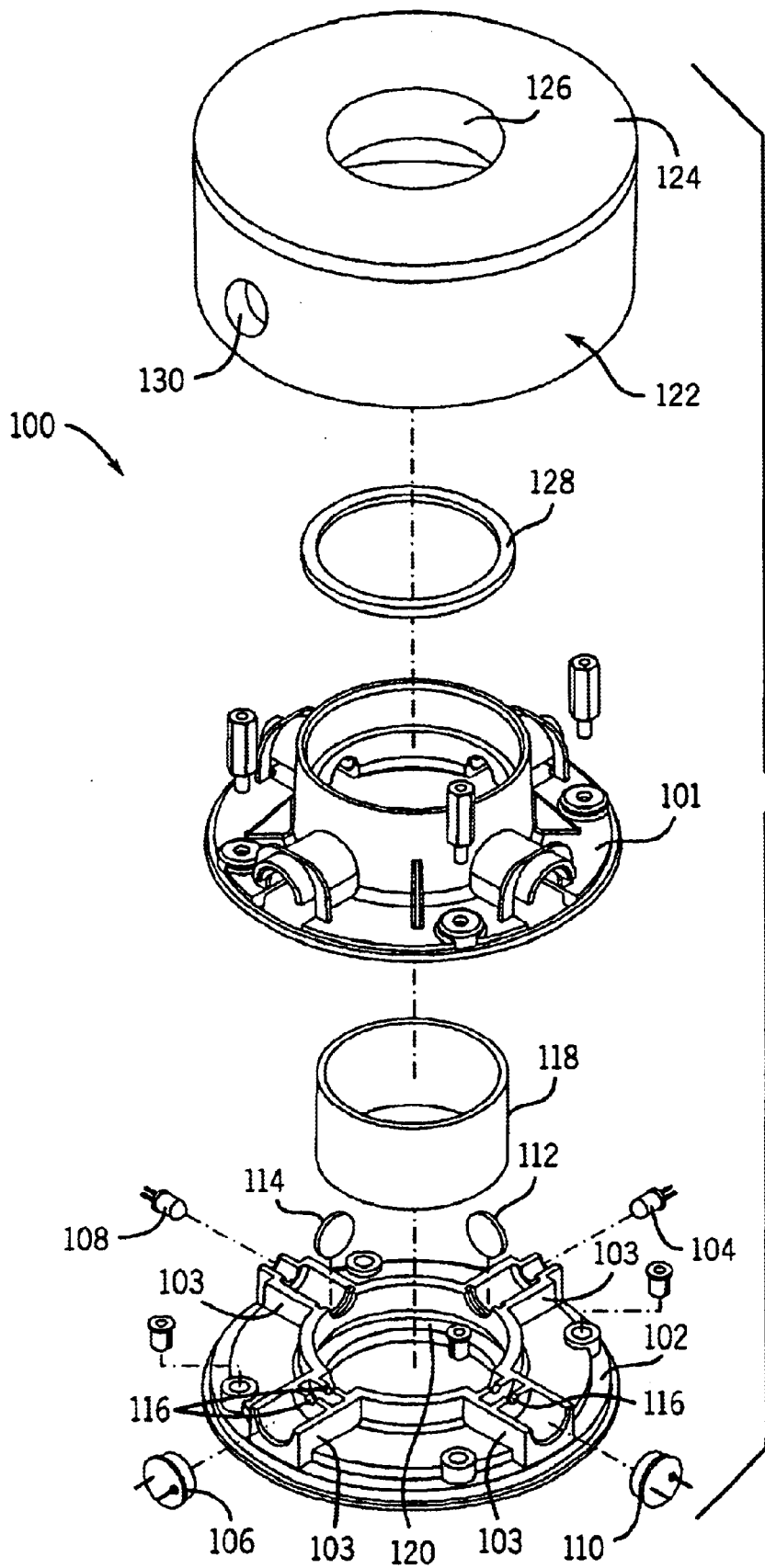
FIG. 6 is an exploded view of a second embodiment of a turbidimeter sensor assembly according to the present invention.

With reference to FIGS. 6 and 7, the present invention can be embodied in a turbidimeter sensor assembly 100 which is designed to examine a liquid flowing through the apparatus. In this embodiment, the turbidimeter sensor assembly 100 has two mounting rings 101 and 102 fabricated of a black polycarbonate material. Each mounting ring 101 and 102 forms mating portions of an annular body that provides four optical component holders 103 spaced radially at 90 degree increments around the rings. The optical component holders 103 receive two light emitter/detector sets. One of those sets comprises a first light emitter 104, such as a light emitting diode, and first light detector 106 in one pair of diametrically opposed holders 103. The other set comprises a second light emitter 108 and a second light detector 110 in the other pair of diametrically opposed holders 103. The two emitters 104 and 108 produce light at a wavelength of 860 nm, for example. A separate disk-shaped lens 112 or 114 is mounted in front of each light emitter 104 or 108, respectively. A pair of field stops 116, in the form of two spaced apart walls with apertures there through, is formed in the mounting rings 101 and 102 in front of each light detector 106 and 110, thereby limiting each detector's field of view. The emitters and detectors face toward the center of the annular body and are held within the respective holder, along with the lenses 112 and 114, when the mounting rings 101 and 102 fit together. The lights rays produced by each emitter 104 and 108 diverge at a fixed angle of 60 degrees. The disk-shaped lens 112 or 114 change that angle of divergence, whereby the light will impinge a transparent lens tube 118 at the proper incident angle so that the light then will be collimated into a non-divergent beam within the central opening of the lens tube.

The transparent lens tube 118 is located within the central opening of the mounting rings 101 and 102, and forms a passage through the sensor assembly 100 for the liquid being examined. The lens tube 118 preferably is made of a scratch resistant material, such as quartz, glass or sapphire, although other substances may be used. The lens tube 118 is held against an inner flange 120 of the second mounting ring 102 thereby forming a liquid tight seal there between. As will be described in greater detail, the lens tube 118 forms a second lens between each emitter and the liquid and additional lenses between the liquid and each detector.

An upper cover 122 extends over the first mounting ring 102 and is attached to the outer circumferential surface of the second mounting ring 102 to form an outer housing of the sensor assembly 100. The upper cover 122, fabricated of black polyvinyl chloride, has a flat top surface 124 with a central aperture about which is an inwardly extending tubular flange 126. In the constructed sensor assembly 100, the tubular flange 126 presses an O-ring 128 against an end of the lens tube 100 to provide a liquid tight seal there between.

The emitters and detectors 104-110 can be connected to the turbidimeter electronics by wires that extend through a fitting threaded into an aperture 130. Alternatively, the electronics can be mounted on an annular printed circuit board inserted into the space 132 in FIG. 7 in which case a cable carrying a turbidity measurement signal would extend through aperture 130.

One will note that the second version of the turbidimeter sensor assembly 100 differs from the first version 10 by the use of lenses 112 and 114 in addition to the lens tube 118. The individual lenses 112 and 114 enable production of a wider light beams passing through the liquid under examination. That is the emitters can produce light rays which diverges at a significantly greater angle (e.g. 60°) than the emitters in the first embodiment (e.g. 6°) in FIGS. 1–3. This greater divergence produces a light beam that has a larger cross sectional area. The individual lenses 112 and 114 redirect the diverging light rays so that they strike the lens tube 118 at the proper angle of incidence to achieve the collimating effect from the lens tube. The refraction of the light rays by the lens tube 118 collimates the light into a non-divergent beam directed through the liquid in that tube. Because this beam is wider than in the first embodiment of the sensor assembly, a greater amount of the liquid is exposed to the light and the sensitivity of the turbidimeter is increased.

The specific configuration of the turbidimeter sensor assembly 100 is a function of the angle at which light diverges from the emitter, the optical characteristics of lenses 112 and 114, the material of the lens tube, and the type of liquid that the turbidimeter is intended to examine. Similar optical expressions as given above for the first embodiment are used to determined the distances from the outer diameter of the lens tube at which to place lenses 112 and 114 and the emitters and detectors.

The sections of the lens tube 100 in front of each light emitter 106 and 107, in conjunction with the liquid in the sample cavity 113, collimates the emitted light rays into a substantially non-diverging beam that is directed toward the diametrically opposed detector 108 and 105, respectively. The sections of the lens tube 100 in front of each light detector 108 and 105 focus the impinging light beam onto the active surface of the adjacent detector.

The foregoing description was primarily directed to a preferred embodiment of the invention. Although some attention was given to various alternatives within the scope of the invention, it is anticipated that one skilled in the art will likely realize additional alternatives that are now apparent from disclosure of embodiments of the invention. Accordingly, the scope of the invention should be determined from the following claims and not limited by the above disclosure.

We claim:

1. An apparatus for measuring turbidity of a liquid, said apparatus comprising:

a lens tube having a curved wall of transparent material and an aperture for receiving the liquid;

a first light emitter positioned adjacent the lens tube to produce a beam of light which diverges at a predefined angle and impinges the wall of the lens tube;

a first light detector positioned adjacent the lens tube diametrically opposite to the first light emitter to produce a signal indicating an intensity of light traveling through the liquid from the first light emitter; and a second light detector positioned adjacent the lens tube to produce a signal indicating an intensity of light from the first light emitter which is scattered upon traveling through the liquid;

wherein the diverging beam of light from the first light emitter is refracted by the lens tube into a collimated beam within the aperture, and light from within the aperture is refracted by the lens tube onto the first light detector and the second light detector.

2. The apparatus as recited in claim 1 further comprising a lens between the first light emitter and the lens tube to redirect the beam of light to strike the lens tube at a predefined angle of incidence.

3. The apparatus as recited in claim 1 wherein the second light detector is spaced substantially ninety degrees around the lens tube from the first light detector.

4. The apparatus as recited in claim 1 further comprising a second light emitter positioned adjacent the lens tube diametrically opposite the second light detector, the second light emitter produces a light beam that diverges at a given angle and impinges the lens tube which refracts the light beam into a collimated beam within the aperture.

5. The apparatus as recited in claim 4 further comprising:
a first lens between the first light emitter and the lens tube for redirecting the beam of light to strike the lens tube at a predefined angle of incidence; and
a second lens between the second light emitter and the lens tube for redirecting the light beam to strike the lens tube at a predetermined angle of incidence.

6. The apparatus as recited in claim 1 wherein the first light emitter, the second light emitter, the first light detector, and the second light detector are spaced at substantially ninety degree increments around the lens tube.

7. The apparatus as recited in claim 1 further comprising an annular housing extending around the lens tube and having a plurality of apertures within each of which one of the first light emitter, the first light detector, and the second light detector is received.

8. The apparatus as recited in claim 7 further comprising a tapered outer tube within which is located the annular housing; and a cap spaced from the annular housing and closing one end of the tapered outer tube.

9. The apparatus as recited in claim 8 further comprising an electrical wire conduit extending within the tapered outer tube from the annular housing through the cap.

10. The apparatus as recited in claim 1 further comprising:
two mounting rings which mate to form an annular body that has four optical component holders spaced radially at 90 degree increments around the annular body; and
a second light emitter received in one of the four optical component holders;
wherein the first light emitter, the first light detector, and the second light detector is received in other ones of the four optical component holders, and the lens tube is located within the annular body.

11. The apparatus as recited in claim 10 further comprising a cover engaging one of the two mounting rings and enclosing the other one of the two mounting rings, the cover having an aperture there through which communicates with the aperture in the lens tube for the transmission of the liquid.

12. A turbidimeter to measure turbidity of a liquid, the turbidimeter comprising:
a lens tube of transparent material having an aperture for receiving the liquid;
a first light emitter positioned adjacent the lens tube to produce a beam of light which diverges at a predefined angle and impinges the lens tube;
a second light emitter positioned adjacent the lens tube to produce a light beam which diverges at a given angle and impinges the lens tube;
a first light detector positioned adjacent the lens tube diametrically opposite to the first light emitter to produce a signal indicating an intensity of light traveling in substantially a straight line through the liquid from the first light emitter; and
a second light detector positioned adjacent the lens tube diametrically opposite to the second light emitter to produce a signal indicating an intensity of light traveling in substantially a straight line through the liquid from the second light emitter;
wherein the diverging beam of light from the first light emitter is refracted by the lens tube into a collimated beam within the aperture, and the diverging light beam from the second light emitter is refracted by the lens tube into another collimated beam within the aperture.

13. The apparatus as recited in claim 12 further comprising:
a first lens between the first light emitter and the lens tube to redirect the beam of light to strike the lens tube at a predefined angle of incidence; and
a second lens between the second light emitter and the lens tube to redirect the light beam to strike the lens tube at a predetermined angle of incidence.

14. The apparatus as recited in claim 12 further comprising an electronic circuit connected to receive signals from the first light detector and the second light detector and in response thereto derive a measurement of the turbidity of the liquid.

15. The apparatus as recited in claim 12 further comprising an annular housing extending around the lens tube and having a plurality of receptacles each of which receiving one of the first light emitter, the second light emitter, the first light detector, and the second light detector.

16. The apparatus as recited in claim 15 wherein the plurality of receptacles are spaced at ninety degree increments around the annular housing.

* * * * *